United States Patent
Benndorf et al.

(10) Patent No.: US 10,278,665 B2
(45) Date of Patent: May 7, 2019

(54) METHOD FOR CONTROLLING AN X-RAY DEVICE AND X-RAY DEVICE

(71) Applicant: SIEMENS HEALTHCARE GMBH, Erlangen (DE)

(72) Inventors: Steffen Benndorf, Roethenbach (DE); Franziska Dinse, Heiligenstadt (DE); Michael Fuhrmann, Herzogenaurach (DE); Jens Hofmann, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 415 days.

(21) Appl. No.: 15/024,460

(22) PCT Filed: Sep. 10, 2014

(86) PCT No.: PCT/EP2014/069254
§ 371 (c)(1),
(2) Date: Mar. 24, 2016

(87) PCT Pub. No.: WO2015/043948
PCT Pub. Date: Apr. 2, 2015

(65) Prior Publication Data
US 2016/0213346 A1    Jul. 28, 2016

(30) Foreign Application Priority Data
Sep. 24, 2013   (DE) ........................ 10 2013 219 193

(51) Int. Cl.
*H05G 1/64*    (2006.01)
*A61B 6/00*    (2006.01)

(52) U.S. Cl.
CPC .............. *A61B 6/54* (2013.01); *A61B 6/4405* (2013.01); *A61B 6/4411* (2013.01); *A61B 6/4452* (2013.01); *A61B 6/4494* (2013.01); *A61B 6/548* (2013.01); *A61B 6/56* (2013.01)

(58) Field of Classification Search
None
See application file for complete search history.

(56) References Cited

U.S. PATENT DOCUMENTS

| | | |
|---|---|---|
| 8,243,883 B2 | 8/2012 | Omernick et al. |
| 8,364,241 B2 | 1/2013 | Hannon et al. |
| 2007/0223649 A1 | 9/2007 | De Godzinsky |
| 2008/0107234 A1 | 5/2008 | Amitani |
| 2009/0084964 A1* | 4/2009 | Kito .......................... G01T 7/00 250/370.08 |
| 2009/0194695 A1 | 8/2009 | Nishino et al. |
| 2011/0013220 A1 | 1/2011 | Sabol et al. |
| 2011/0075813 A1 | 3/2011 | Venturino et al. |

(Continued)

FOREIGN PATENT DOCUMENTS

| | | |
|---|---|---|
| DE | 102010061569 A1 | 12/2011 |
| EP | 2390682 A2 | 11/2011 |

*Primary Examiner* — Hoon K Song
(74) *Attorney, Agent, or Firm* — Laurence Greenberg; Werner Stemer; Ralph Locher

(57) ABSTRACT

A method controls an X-ray apparatus which contains a base station and at least one X-ray detector, wherein status information about the at least one X-ray detector is obtained. The status information is deposited in a database of the base station and the X-ray apparatus is controlled on the basis of the status information from the database.

12 Claims, 8 Drawing Sheets

(56) References Cited

U.S. PATENT DOCUMENTS

2011/0116486 A1* 5/2011 Tachikawa ............ A61B 6/4494
                                                                         370/338
2011/0274251 A1   11/2011 Omernick et al.
2013/0094628 A1* 4/2013 Lalena ................. A61B 6/4283
                                                                         378/98

\* cited by examiner

| X-ray detector ID | Transfer quality | Image status | Battery |
|---|---|---|---|
| 456 | Very good | 0 | 77% |
| 123 | Critical | 1 | 98% |
| 2a¹ | Error | 1 | 46% |

METHOD FOR CONTROLLING AN X-RAY DEVICE AND X-RAY DEVICE

BACKGROUND OF THE INVENTION

Field of the Invention

X-ray devices comprising one or more portable x-ray detectors which have a data connection to a base station of the x-ray device by way of a wireless interface are known. In this way, an x-ray detector can be e.g. oriented freely in space or placed in a detector holder at a recording location for the purposes of x-ray imaging. For the purposes of improved handling, one or more x-ray detectors can be interchanged between different x-ray devices—to this end, the x-ray detector can then be registered and deregistered to and from base stations of the various x-ray devices. Moreover, the x-ray device with the portable x-ray detectors may require less space.

However, such x-ray devices have a number of disadvantages. By way of example, there may be ambiguities in the operation due to the flexible assignment between an x-ray detector and a base station, for example in a situation in which a plurality of x-ray detectors and/or base stations are present. Moreover, compared with e.g. a wired interface, the wireless interface may have a reduced reliability in the data transmission.

By way of example, such disadvantages can cause a radiation exposure process or image acquisition process to be carried out incorrectly or not be completed successfully, which may unnecessarily increase a radiation exposure of a subject and/or staff as result of a radiation dose. By way of example, an incorrect radiation exposure process may occur in a scenario in which no x-ray detector is present at a specific recording location and/or if a radiation exposure is carried out in relation to an x-ray detector which is not registered to a specific base station.

Phrased more generally, ambiguities may arise in respect of the combinations of a plurality of available x-ray detectors, which may be registered to a base station. In particular, this can relate to a registration process and/or a deregistration process of the corresponding x-ray detectors to and from the base station and/or the assignment of a specific recording location to the x-ray detectors. By way of example, this can result in a mistaken or incorrect radiation exposure, as a result of which a radiation exposure of a subject may be unnecessarily increased.

By way of example, ambiguities which are selected from the following group may arise: uncertainty as to where an x-ray detector may be used; uncertainty as to the x-ray images for which an x-ray detector may be used; uncertainty as to the x-ray images for which an x-ray detector is already registered; uncertainty as to whether other x-ray detectors are already registered to a base station; uncertainty as to where x-ray detectors which are registered to a base station are located; uncertainty as to how many x-ray detectors are registered to a base station; uncertainty as to the position at which an x-ray detector is situated; uncertainty as to whether a transmission quality of a wireless interface of a specific x-ray detector has a sufficient quality; uncertainty as to whether an unused x-ray detector which has a comparatively low battery status can be interchanged with another x-ray detector in order to carry out a charging process of the battery of the corresponding x-ray detector while the interchanged x-ray detector is used for the acquisition of an x-ray image; uncertainty as to whether a specific recording location is occupied by two x-ray detectors; uncertainty as to whether a specific x-ray detector is registered to a specific base station; uncertainty as to which x-ray detectors from a multiplicity of x-ray detectors are already registered to a base station and/or configured for a specific recording location; uncertainty as to whether a specific x-ray detector can even be registered to a base station; uncertainty as to which x-ray detector of a multiplicity of x-ray detectors is the currently active x-ray detector; etc.

BRIEF SUMMARY OF THE INVENTION

Therefore, there is a need for improved x-ray devices comprising a base station and at least one wirelessly connected x-ray detector. In particular, there is a need for such x-ray devices which ensure a reliable and failsafe handling.

This object is achieved by the features of the independent claims. The dependent claims define embodiments.

According to one aspect, the invention relates to a method for controlling an x-ray device comprising a base station and at least one x-ray detector. The base station is configured to receive an acquired x-ray image from the x-ray detector by way of a wireless interface. The method comprises obtaining status information about the at least one x-ray detector. The status information relates to an operating parameter of the at least one x-ray detector. The method furthermore comprises storing the status information in a database of the base station. The database has at least one entry for each one of the at least one x-ray detector. The method furthermore comprises controlling the x-ray device on the basis of the status information from the database.

By way of example, the x-ray detector can be configured to acquire one or more x-ray images of a subject and transmit these to the base station via the wireless interface. Accordingly, the base station can be configured to receive the one or more x-ray images from the x-ray detector. The x-ray detector can be, for example, portable, as a result of which a user is e.g. able to position the latter with respect to the subject. However, it would also be possible for the at least one x-ray detector to be securely attached, for example to a wall or in a couch. By way of example, portable x-ray detectors can be affixed in a detector holder which, for example, is integrated at a wall or in a couch for a subject. The detector holder can describe a recording location.

It would be possible for a specific x-ray detector to be registered to a plurality of base stations. By way of example, it would be possible for various x-ray detectors which are registered to a base station to be securely connected to the latter and for others to be portable.

By way of example, the wireless interface can be selected from the following group: wireless local area network (WLAN), telephone network, Bluetooth. In general, the wireless interface can have e.g. a range of the order of several ten meters.

By way of example, the status information can characterize a current operating state of the at least one x-ray detector. In this case, different x-ray detectors can have different or similar operating parameters. The status information can relate to very different operating parameters, for example operating parameters in respect of an identification, available resources, operating statistics, activated and/or deactivated operating features and/or an error indication for the at least one x-ray detector.

By way of example, the status information can be obtained within the scope of a specific data exchange protocol. By way of example, the status information can be received by way of the wireless interface. Alternatively or additionally, it would also be possible for the status information to be obtained by way of a user interface of the base station by means of user entries. In other words, the status information can be, for example, automatically provided by the x-ray detector itself, or else it can be provided by a user of the x-ray device. In a simple scenario, the x-ray detector could be affixed e.g. at a specific recording location by way of a detector holder; the user can then input the corresponding status information, which specifies the recording location (positional specification), by way of the user interface or this could be carried out automatically.

Storing the status information in the database can correspond to, for example, targeted storing of the status information in a corresponding entry in the database. The stored data could have very different structures. By way of example, the database can be structured in respect of the at least one x-ray detector. However, alternatively or additionally, it also would be possible for the database to be structured in respect of various other operating parameters of the at least one x-ray detector. It would also be possible for the database to be structured in respect of one or more users of the x-ray device. By way of example, the database can be stored in an internal memory of the base station or in a central memory, in respect of which the base station has read and write access.

Controlling the x-ray device on the basis of status information can mean e.g. the following: carrying out a user interaction which at least partly resorts to the status information from the database, for example by way of the user interface; and/or transmitting at least one control command to the at least one x-ray detector, wherein the at least one control demand depends on the status information from the database and/or wherein said control command is created in a manner dependent on the status information from the database. By way of example, in a simple scenario, a dialog box could be created within the scope of controlling the x-ray device, which dialog box uses status information from the database at least in part; the x-ray device could be controlled by the dialog box by way of a user interaction. In a further simple scenario, there could be e.g. direct control of the x-ray device, i.e. without user interaction.

What can be achieved by the availability of the database is that the operating parameters of the at least one x-ray detector are stored and accessible in the base station in a current and clear manner. What can be achieved thereby is that ambiguities when controlling the x-ray device can be reduced or avoided. Errors in the operation can be reduced and prevented and an unnecessary radiation exposure can be reduced. The user interaction can be designed more clearly.

By way of example, the status information can comprise an identification number of the at least one x-ray detector. By way of example, it is possible for the method to furthermore comprise: within the scope of the registration process of the at least one x-ray detector to the base station: receiving the status information from the at least one x-ray detector by way of a further wireless interface, which differs from the wireless interface and has a smaller range than the wireless interface.

A manual input of the identification number by the user within the scope of the registration process can be dispensed with. By way of example, the identification number can uniquely identify a specific x-ray detector to differentiate it from further x-ray detectors. By way of example, the identification number can be a number code or, for example, an alphanumeric code. By way of example, the identification number can correspond to a serial number or represent a user-defined designation.

If no corresponding entry for a specific x-ray detector is present in the database, this may mean that this specific x-ray detector is not registered to the base station. However, if a corresponding entry for the specific x-ray detector is already present in the database, this may mean that this specific x-ray detector is registered to the base station. Correspondingly, the registration process (a deregistration process) can denote the creation (the deletion) of the corresponding entry for this specific x-ray detector in the database. Naturally, it may also be possible to store specific status information in the base station for deregistered, e.g. previously registered, x-ray detectors, as a result of which e.g. the registration process can be designed more easily or more quickly.

By way of example, the range of the wireless interface or of the further wireless interface can denote that spatial region in relation to the corresponding transceiver within which a comparatively reliable data transfer is possible via the corresponding wireless interface. By way of example, if no data transfer or only particularly restricted data transfer is possible by way of the wireless interface (restricted connectivity), the x-ray detector might be situated outside of the range of the wireless interface, for example in relation to a transceiver situated in the base station. In general, the transfer by means of the wireless interface can be bidirectional. The further wireless interface can be unidirectional or bidirectional. If the further wireless interface is unidirectional, it is possible, for example, to transfer data from the x-ray detector to the base station. In other words, both the x-ray detector and the base station may each comprise a transceiver for the wireless interface and/or the further wireless interface. The transceiver can be configured to transmit and/or receive data. Corresponding arguments, as explained above in relation to the range, apply accordingly to both transceivers.

By way of example, the range of the further wireless interface may be a few centimeters or less than one meter. By way of example, it would be possible for the further wireless interface only to be able to ensure data transfer within the scope of a clear direct connection (visual connection) between the two transceivers in the base station and the x-ray detector.

In other words, within the scope of the registration process, it may be necessary to arrange the x-ray detector and the base station close to one another due to the comparatively small range of the further wireless interface. In this way, ambiguities within the scope of the registration process of the at least one x-ray detector can be reduced or removed. It can immediately be clear to the user at which base station a specific x-ray detector is registered. By way of example, such ambiguities can relate to the following points: where or to which base station is the x-ray detector registered; how is the x-ray detector registered; is there an option for restoration when registering the x-ray detector; how can a successfully carried out registration process be verified? At the same time, comparatively quick carrying out of the registration process can be ensured without, however, opening further error sources within the scope of the registration process.

In contrast to various reference implementations, the above-described techniques can prevent e.g. there being an incorrect input of the identification number, for example by a user. At the same time, the exchange of the identification number can be carried out quickly, for example compared to a manual input. Moreover, there can be a check of the identification number, for example by way of a further data transfer and/or by reproducing the corresponding information for the user. Consciously carrying out the registration process by the user can be ensured.

Corresponding techniques, as were explained above in relation to the registration process, can also be applied to the deregistration process of the at least one x-ray detector.

By way of example, it would also be possible for various detector holders for portable x-ray detectors to each have an associated identification number. Then, an association between the identification number of the detector holder, to which a specific x-ray detector has been attached, and this x-ray detector can be comprised by the status information and stored in the database.

By way of example, the method may furthermore comprise: within the scope of the registration process of the at least one x-ray detector to the base station: transmitting the status information, which comprises the identification number of the at least one x-ray detector, to the at least one x-ray detector by way of the wireless interface.

By transmitting the status information, which comprises the identification number of the at least one x-ray detector, from the x-ray detector to the base station and from the base station to the x-ray detector, it is possible to ensure an increased degree of reliability during the registration process. Errors in the transfer can be identified and corrected.

By using the further wireless interface it is possible, in particular, to bring about a conscious registration process by the user, for example by virtue of the user necessarily arranging the x-ray detector to be registered within the comparatively small range of the further wireless interface in relation to the base station.

By way of example, the further wireless interface can be selected from the following group: infrared, Bluetooth, near field communication (NFC), optical transmission of machine-readable signs.

By way of example, the machine-readable sign may be a barcode or a quick response (QR) code. In other words, the further wireless interface can be an optical interface, in which passive identification markers, which are e.g. affixed to an outer surface of the x-ray detector, are acquired, e.g. by a camera or a barcode reader in the base station. In this case, visual connection may be required by the further wireless interface.

By way of example, the status information can comprise a position specification of the at least one x-ray detector. The at least one x-ray detector can be portable. The position specification can be set in respect of a detector holder, in which the portable x-ray detector can be affixed. By way of example, the detector holder can be integrated in a wall apparatus or in a couch for a subject. The detector holder may have corresponding dimensions such that the portable x-ray detector can be held substantially completely in the detector holder. By way of example, the position specification in respect of the detector holder can be characterized e.g. in respect of the location of the detector holder in an examination room, or else in respect of the type of detector holder, i.e., for example "table detector holder" or "wall detector holder". By way of example, it would be possible for one and the same x-ray detector to be able to be placed in different detector holders.

By way of the position specification, a user of the x-ray device can be informed quickly and in a hardly error-prone manner about a current or sought-after position of a specific x-ray detector, for example by way of the user interface. As a result of this, it is possible, for example, to avoid errors when controlling the x-ray device, which may arise, for example, by mistaken actuation of an x-ray detector. By way of example, it is possible by way of a user interface to provide a user of the x-ray device with an overview, which lists the various x-ray detectors registered to a base station with the associated position specification. As a result of this, it may be possible for a user quickly to find out within the scope of the registration process at which—still free— position a further x-ray detector can be registered.

By way of example, it may be the case that not every detector holder is able to receive every x-ray detector. By way of example, there may be large and small x-ray detectors. By way of example, a specific detector holder can affix either small x-ray detectors or large x-ray detectors. By way of example, it would be possible for the position specification of the status information to contain corresponding information. As a result of this, it may be possible, for example, that the information as to whether a specific x-ray detector with a specific position specification is a large or a small x-ray detector is provided to a user via the user interface.

By way of example, the status information can comprise at least one element selected from the following group: a battery charge state of the at least one x-ray detector, a number of buffered and acquired x-ray images in the at least one x-ray detector, a status of an acquisition process of the x-ray image, a transmission quality of the wireless interface, calibration data, calibration metadata, an identification number of the at least one x-ray detector, a position specification of the at least one x-ray detector, a detector type of the at least one x-ray detector.

By way of example, particularly in the case where the at least one x-ray detector is a portable x-ray detector, the latter may have a battery with the associated battery charge state. The x-ray detector can furthermore comprise a buffer data memory, in which acquired x-ray images can be buffered before they are transmitted to the base station for further processing by a user. By way of example, the status of the acquisition process may relate to: the acquisition process is prepared; the acquisition process is currently being carried out; the acquisition process is successfully completed, waiting for transfer of the x-ray image; the acquisition process is successfully completed, the x-ray image is currently being transferred to the base station.

By way of example, the transfer quality of the wireless interface can relate to a signal level of the wireless interface. The calibration data of the x-ray detector can e.g. contain specific parameters, on the basis of which the x-ray image is acquired. By way of example, the calibration data can comprise parameters of the beam path of the x-ray beams, optical properties of the x-ray detector and/or of the x-ray source. By way of example, the calibration metadata can denote a currentness and/or a necessity for new calibration data in relation to a specific base station and/or a compatibility of the calibration data with an x-ray detector type. By way of example, the calibration data can be stored in the base station and/or in the x-ray detector. By way of example, the calibration data and/or the calibration metadata can be transferred to other base stations by means of a universal serial bus (USB) interface and/or a wireless data connection corresponding to the wireless interface. Accordingly, it would be possible for the x-ray detector to provide the corresponding calibration data of different base stations, to which it is registered, by way of the wireless interface if the calibration data are stored on an x-ray detector.

By way of example, if the status information comprises the transfer quality of the wireless interface and/or the battery charge state, it may be possible to inform the user of the x-ray system about the current status in this respect, in each case via the user interface.

By way of example, controlling the x-ray device can furthermore comprise: transmitting a control command to the at least one x-ray detector by way of the wireless interface, wherein the control command requests transmission of an x-ray image from the x-ray detector by way of the wireless interface.

By way of example, the control command can simultaneously request the acquisition of the x-ray image by the x-ray detector. However, it would also be possible, for example, for the control command requesting the transmission of the x-ray image to be sent as a reaction to a corresponding notification by the x-ray detector indicating that an acquired x-ray image is buffered in a buffer of the x-ray detector. This control command could also be triggered by the user by way of the user interface.

Depending on the transmission of the control command, the method can furthermore comprise: checking whether the acquired x-ray image is received by way of the wireless interface. Furthermore, if the acquired x-ray image is not received, the method can also comprise: operating the x-ray device in an error mode in respect of the at least one x-ray detector, which error mode serves to improve the connectivity between the base station and the at least one x-ray detector.

Checking can comprise e.g. a clock and/or error correction protocols of the wireless interface. By way of example, the connectivity can denote the ability to successfully transfer data by way of the wireless interface. By way of example, the x-ray image may have a comparatively large amount of data—for example in relation to the control command—such that a probability of the x-ray image not being transferred successfully may be significant if the transfer quality of the wireless interface is comparatively low. By way of example, the connectivity may depend on the transfer quality. However, alternatively or additionally, the connectivity may depend on settings of the wireless interface itself, such as e.g. service quality parameters, signal level and so on.

Various measures which serve to rectify errors can be comprised in the error mode, for example in a specific sequence. By way of example, within the scope of operating the x-ray device in the error mode, it would be possible for the user of the x-ray device to be provided with one or more of the following items of information via a user interface: whether something is currently happening; what is currently happening; where the x-ray image is currently situated; whether there currently is a problem anywhere; whether a possible problem can be rectified by the user; how the possible problem can be rectified by the user; what the next steps that the user should undertake are; how the user could leave the situation. By way of example, the notification to have the x-ray detector come closer to the base station can be communicated to the user via the user interface. That is to say, in this way it would be possible, for example, to increase the transfer quality of the wireless interface, as a result of which the connectivity can be restored. Via the user interface, the user could be provided with currently updated information about the current transfer quality of the wireless interface. In this way, the user could identify whether the transfer quality in fact improves when he moves the x-ray detector.

By way of example, it would be possible for the error mode to be terminated when the x-ray image was successfully received by the base station. Alternatively or additionally, the error mode can be terminated e.g. following a user input. There can also be other termination criteria for the error mode. In general, it is possible for the error mode to be terminated by a user and/or in an automated manner at any time. However, it would also be possible, for example, for the error mode to be started manually by the user himself via the user interface.

By way of example, the following information could be provided to the user in the error mode: the x-ray device is currently operated in the error mode; an attempt is currently being made to transfer the x-ray image; the connectivity could be improved by various user actions, for example by virtue of the x-ray detector being brought more closely to a transceiver of the wireless interface or closer to the base station; the request to bring the x-ray detector closer to a transceiver of the wireless interface; the request to replace a battery of the x-ray detector; the request to contact a service technician in order to rectify the problem; the display of the current transfer quality of the wireless interface; etc.

By way of example, if the x-ray device is operated in the error mode in relation to the at least one x-ray detector, the method may furthermore comprise: transmitting a further control command to the at least one x-ray detector, which control command blocks the at least one x-ray detector in respect of future registrations to base stations and/or re-initializes the at least one x-ray detector.

By way of example, the above-described transmission of the further control command can be carried out after several unsuccessful attempts of transferring the x-ray image by way of the wireless interface. By way of example, the re-initialization can be carried out after a user of the x-ray device has confirmed that the x-ray detector is situated in the vicinity of a transceiver of the wireless interface and the battery charge state of a battery of the x-ray detector is greater than the threshold. This can comprise an automatic restart of the relevant system components of the x-ray detector within the scope of the re-initialization of the x-ray detector. Subsequently, the transfer of the acquired x-ray image by way of the wireless interface can be carried out again. If the transfer of the x-ray image by way of the wireless interface is not successful in this case either, the x-ray detector can be blocked in respect of registrations to base stations. Accordingly, a request to request a service technician for servicing the x-ray detector can be output to the user by way of the user interface.

By way of example, within the scope of operating the at least one x-ray detector in the error mode, the at least one x-ray detector can continue to be blocked in respect of future acquisition of x-ray images. By way of example, it would be possible for such a block of the at least one x-ray detector not to be circumventable by the user. By way of example, it is thereby possible to prevent a further x-ray image from being acquired by an x-ray detector which is most probably defective, which image then could not be used under certain circumstances. In this way, the potential of unnecessary radiation exposure of the subject can be further reduced.

By way of example, if the x-ray device is operated in the error mode in relation to the at least one x-ray detector, the method may furthermore comprise: repeated reception of status information, which relates to a transmission quality of the wireless interface, and output of the transmission quality to the user. By way of example, the transfer quality can be output continuously to the user. As a result of that, it may be possible for the user to immediately obtain a response as to whether, for example, moving the portable detector is relevant to improving the transfer quality for reestablishing the connectivity between the base station and the at least one x-ray detector.

By way of example, if the x-ray device is operated in the error mode in relation to the at least one x-ray detector, the method may furthermore comprise: receiving status information from the at least one x-ray detector by way of the wireless interface, wherein the status information comprises a number of buffered and acquired x-ray images in the at least one x-ray detector and/or a status of an acquisition process of the x-ray image.

In other words, the received status information can comprise metadata of an x-ray image. In this way, it is also possible to inform the user of the x-ray device in a comprehensive and current fashion about the current operating state of the various components of the x-ray device.

It should be understood that, in general, the status information has a comparatively small file size compared to the x-ray images to be transferred. Therefore, a probability of status information being transferred successfully by way of the wireless interface can be comparatively high, in particular in relation to a probability of the x-ray image being transferred successfully. By way of example, in the case of a specific transfer quality, it may just still be possible to transfer the comparatively small status information successfully by way of the wireless interface, while a successful transfer of the x-ray image by way of the wireless interface is not possible or only possible to a restricted extent.

By way of example, the controlling can furthermore comprise carrying out a user interaction, wherein the user interaction comprises depicting status information from the database on a monitor and/or obtaining status information by a user input.

By way of example, the user interaction could comprise some or all of the following steps in various combinations: after the successful registration process of a specific x-ray detector using the further wireless interface, which may be e.g. an infrared interface, there can be a manual confirmation of the recording location in a dialog box for setting a position specification of the x-ray detector. By way of example, it may be the case that, during the registration process of an x-ray detector, the user of the x-ray device actively decides the position at which the x-ray detector to be registered is intended to be used. Accordingly, it can be possible for the user to set where the x-ray detectors previously already registered to the x-ray device are intended to be used. By way of example, a change of the previous selection can be possible in a corresponding dialog of the user interface. The dialog can prevent a double registration of a plurality of x-ray detectors, for example at the same detector holder. As a result of such a concept, a comprehensive consistency check can be ensured within the scope of the registration process; by way of example, it is possible to prevent double occupancy of a specific detector holder and it is possible to ensure that there are no empty detector holders. Additionally, x-ray detectors in present detector holders can be identified. By way of example, a quick registration could thereby be possible: recording locations can be preset in the dialog of the user interaction, as a result of which the position specification can be obtained.

By installing an additional safety functionality, it is also possible to ensure that the x-ray detectors are used differently than in the way in which they are registered. By way of example, by identifying the detector holder in which a specific x-ray detector situated, the system can obtain feedback in respect of the x-ray detector at which an x-ray source is aligned. In the case of additional position sensors being available for the x-ray detectors, it is also possible to identify the precise room location and the position of an x-ray detector in an examination room. As a result of this, further effects can be obtained. Thus, for example, it is possible to depict an overview graphic so that a user of the x-ray device finds the x-ray detectors more easily. Even in the case of free recordings, i.e. using x-ray detectors which are not situated in an x-ray detector holder, the information as to whether an x-ray source is aligned onto an x-ray detector and as to whether the corresponding x-ray detector is also active would also be available.

Checking the current recording location of the various x-ray detectors and changing these settings can be undertaken at any time in the overview menu of the user interaction.

By way of example, the user can obtain the further following information in the overview menu: which x-ray detector is in the vicinity, for example depending on the transfer quality of the wireless interface; transfer quality of the wireless interface of the various registered x-ray detectors; battery status of the various registered x-ray detectors (by way of example, this is expedient for the decision as to whether it is still worth using an x-ray detector for a free recording or whether the respective x-ray detector is preferably replaced by another x-ray detector which has a higher battery charge state); displaying an identification number of the various registered x-ray detectors; displaying graphics as to whether this relates to a specific type of x-ray detector, e.g. whether this relates to a small or a large x-ray detector; the possibility of deregistering a specific x-ray detector from the x-ray device; displaying whether already acquired but not transferred x-ray images are buffered on the x-ray detector, with the option of initiating a new transfer attempt for the buffered x-ray images. An actuatable button can be created in the dialog of the user interaction for each registered x-ray detector, by means of which button the respective x-ray detector can be deregistered directly. As an additional function for the detector identification, it may be possible in the dialog of the user interaction to click on the corresponding x-ray detector and to obtain corresponding acoustic and/or visual feedback from the x-ray detector, for example by means of a beep. As a result, the user of the x-ray device can obtain direct feedback regarding which x-ray detector the x-ray detector clicked in the dialog is. As a result of this, it is also possible, for example, to check whether a specific x-ray detector is attached to the correct detector holder or whether the stored position specification of the status information applies. As an additional function, it may be possible for the user himself to check on the x-ray device as to whether this relates to the currently active x-ray detector. Whether a specific x-ray detector is registered to the x-ray device could also be transferred by way of the wireless interface. It would also be possible for a query to be started by a user pressing a button on an x-ray detector and for the user to obtain feedback, e.g. by way of the user interface 103. In general, this feedback can be provided at the recording location, i.e. at the x-ray detector itself, and/or at the base station. By way of example, it would be possible for the above-described overview menu to open automatically and to automatically close itself again after a specific period of time, for example after ten seconds, for example following a registration of an x-ray detector. By way of example, as an alternative or in addition to the overview menu, it would be possible to provide further status indications by way of the user interface. By way of example, such status indications can indicate various operating parameters of an x-ray detector and, for example, the current transfer quality of the wireless interface, the battery charge state or an icon with the information that a specific portable x-ray detector is used.

Situations in which a user has two or more x-ray detectors registered to an x-ray device for free recordings may arise.

It would be possible, for example, for him to change over between these at the recording location, i.e. by way of a user input at the x-ray detectors. Additionally, the changeover between the various x-ray detectors can also be carried out at the base station. By way of example, the changeover could be implemented by a pop-up menu at the user interface. Here too, the assignment of the various x-ray detectors could be carried out by way of corresponding icons.

By way of example, the method can also comprise monitoring for changes in the status information from the database, and in the case of changes in the status information from the database: outputting corresponding information to a user.

In this way, the user can always have up-to-date information about the various operating parameters.

In accordance with a further aspect, the invention relates to an x-ray device comprising a base station and at least one x-ray detector. The base station can be configured to receive an acquired x-ray image from the x-ray detector by way of a wireless interface. The base station can comprise a computer unit configured to carry out the following steps: obtaining status information about the at least one x-ray detector, wherein the status information relates to an operating parameter of the at least one x-ray detector; and storing the status information in a database of the base station, wherein the database has at least one entry for each one of the at least one x-ray detector; and controlling the x-ray device on the basis of the status information from the database.

By way of example, the x-ray device in accordance with the aspect currently under discussion can be configured to carry out a method for controlling an x-ray device in accordance with a further aspect of the present invention.

It is possible to obtain effects for such an x-ray device which are comparable with the effects which can be obtained for the method for controlling the x-ray device in accordance with a further aspect of the present invention.

The features presented above and features described below can be used not only in the corresponding explicitly presented combinations, but also in further combinations or in isolation, without departing from the scope of protection of the present invention.

The above-described properties, features and advantages of this invention and the manner in which they are achieved become clearer and more easily understandable in conjunction with the following description of the exemplary embodiments, which are explained in more detail in conjunction with the drawings.

DESCRIPTION OF THE INVENTION

Below, the present invention is explained in more detail on the basis of preferred embodiments, with reference being made to the drawings. In the figures, the same reference signs denote the same or similar elements.

The following description of exemplary embodiments with reference to the figures should not be construed as limiting. The figures are purely illustrative.

Below, the present invention is explained in more detail on the basis of preferred embodiments, with reference being made to the drawings. In the figures, the same reference signs denote the same or similar elements. The figures are schematic representations of various embodiments of the invention. Elements depicted in the figures are not necessarily depicted true to scale. Rather, the various elements depicted in the figures are reproduced in such a way that the function and general purpose thereof becomes clear to a person skilled in the art. Connections and couplings between functional units and elements depicted in the figures can also be implemented as indirect connections or couplings. A connection or coupling can be implemented in a wired or wireless fashion unless anything else is explicitly stated. Functional units can be implemented as hardware, software or a combination of hardware and software.

Figure 1:
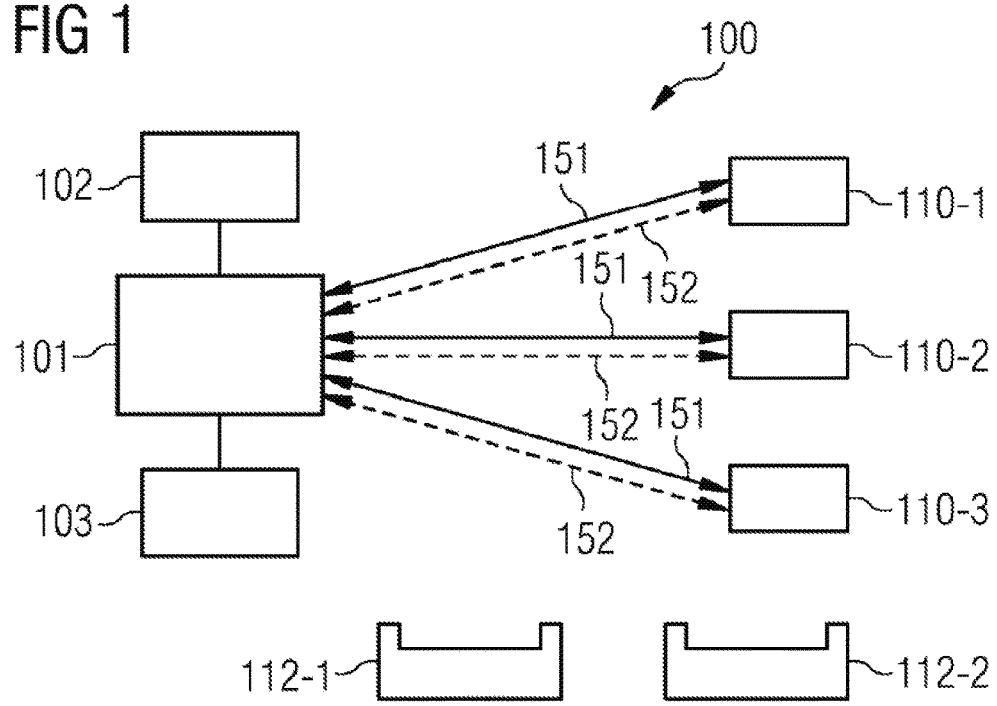
FIG. 1 is a schematic view of an x-ray device with three x-ray detectors and a base station.

FIG. 1 depicts an x-ray device 100. The x-ray device 100 comprises a base station 101 and three registered x-ray detectors 110-1, 110-2, 110-3. The x-ray device 100 could also comprise a greater or fewer number of x-ray detectors 110-1, 110-2, 110-3 since, in this respect, it has a modular design. Each one of the x-ray detectors 110-1, 110-2, 110-3 and the base station 101 comprise a transceiver, which is configured to establish a wireless interface 151 for bidirectional data transfer between these units. Moreover, a further wireless interface 152 is established between each one of the x-ray detectors 110-1, 110-2, 110-3 and the base station 101. By way of example, x-ray images acquired by the x-ray detectors 110-1, 110-2, 110-3 and/or status information about the respective x-ray detector 110-1, 110-2, 110-3, which relates to an operating parameter of the at least one x-ray detector 110-1, 110-2, 110-3, can be transferred by way of the wireless interfaces 151, 152.

The x-ray device 100 furthermore comprises an x-ray source 102. The base station 101 can actuate the x-ray source 102 in such a way that the x-ray source 102 emits x-ray beams. These emitted x-ray beams can be acquired as the x-ray image by an x-ray detector 110-1, 110-2, 110-3 after transmission through a subject.

By way of example, the various x-ray detectors 110-1, 110-2, 110-3 can be integrated securely in other elements, for example in an examination table, on which the subject can be arranged, or in a wall unit of the x-ray device 100, or they can be portable for free positioning. In the case of the portable x-ray detectors 110-1, 110-2, 110-3 in particular, the latter can be affixed in a detector holder 112-1, 112-2; to this end, the x-ray detectors 110-1, 110-2, 110-3 can be inserted into one of the detector holders 112-1, 112-2.

The x-ray device 100 also comprises a user interface 103 which, for example, can comprise one or more of the following elements: a monitor, a touch-sensitive monitor, keyboard, a mouse, loudspeakers, voice recognition, gesture recognition, a graphic user interaction with dialog boxes, etc. By way of the user interface 103, it is possible to output information to a user of the x-ray device 100 or information can be obtained by the user of the x-ray device 100. By way of example, status information in respect of one of the x-ray detectors 110-1, 110-2, 110-3 can be obtained by way of the user interface 103. By way of example, the user can specify a position specification of one of the x-ray detectors 110-1, 110-2, 110-3, for example in respect of one of the detector holders 112-1, 112-2.

Figure 2:
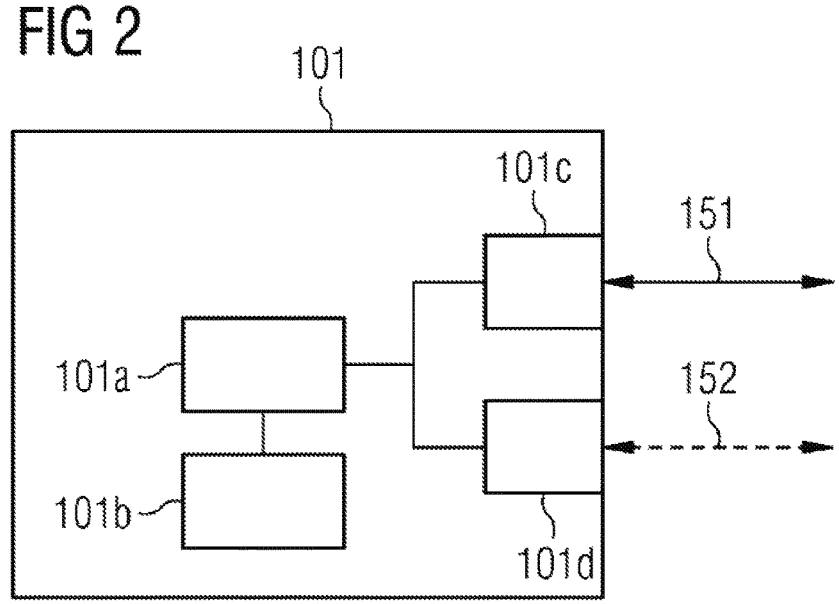
FIG. 2 illustrates the base station in more detail.

The base station 101 of the x-ray device 100 is depicted in more detail in FIG. 2. FIG. 2 illustrates a respective transceiver 101c, 101d for the wireless interfaces 151, 152. The transceivers 101c, 101d have a data connection to a computer unit 101a of the base station 101. The computer unit 101a can access a database 101b, which e.g. is stored in a physical memory. Status information relating to an operating parameter of an x-ray detector 110-1, 110-2, 110-3 and, for example, obtained by way of one of the wireless interfaces 151, 152 and/or by way of the user interface 103 (not depicted in FIG. 2) are stored in the database 101b of the base station 101. The database 101b has at least one entry for each one of the x-ray detectors 110-1, 110-2, 110-3. The computer unit 101a is configured to control the x-ray device 100 on the basis of the status information from the database 101b. By way of example, controlling can relate to the acquisition of x-ray images and/or output and reception of information by way of the user interface 103.

Figures 3, 4:
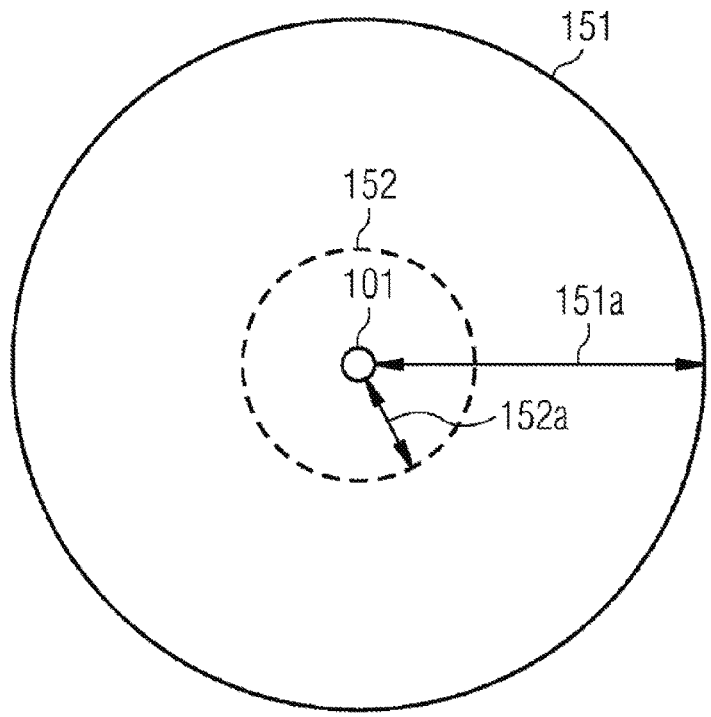
FIG. 3 illustrates a database in which various operating parameters of the three x-ray detectors are stored.
FIG. 4 illustrates a range of a wireless interface and a further wireless interface for data transfer between the base station and the x-ray detectors.

FIG. 3 depicts the database 101b. Status information 190-0, 190-1, 190-2, 190-3 is stored in each case for the three x-ray detectors 110-1, 110-2, 110-3. By way of example, the status information 190-0 comprises an identification number of the various x-ray detectors 110-1, 110-2, 110-3, which, for example, can be received within the scope of a registration process of the respective x-ray detectors 110-1, 110-2, 110-3 to the base station 101 by way of the further data interface 152. The status information 190-1 comprises a transfer quality of the wireless interface 151. The status information 190-2 comprises the status of an acquisition process of the x-ray image by virtue of there being a binary indication as to whether an x-ray image was successfully acquired and whether it is buffered in a buffer of the respective x-ray detector 110-1, 110-2, 110-3. Status information 190-3 comprises a battery charge state of the respective x-ray detector 110-1, 110-2, 110-3.

Naturally, the status information 190-0, 190-1, 190-2, 190-3 in FIG. 3 is purely illustrative. It is possible to describe other or further operating parameters by way of the respective status information 190-0, 190-1, 190-2, 190-3. By way of example, the status information 190-0, 190-1, 190-2, 190-3 could also, alternatively or additionally, comprise a number of buffered and acquired x-ray images in the various x-ray detectors 110-1, 110-2, 110-3, calibration data or calibration metadata or a position specification of the x-ray detectors 110-1, 110-2, 110-3. However, it would also be possible for the resolution or the manner in which the various items of status information 190-0, 190-1, 190-2, 190-3 indicate the respective operating parameter to deviate from the variants depicted in FIG. 3. By way of example, the battery charge state 190-3 could be specified not by way of a percentage specification but rather by way of values such as "full", "half-full" and "empty". By way of example, if the status information 190-0, 190-1, 190-2, 190-3 relates to a position specification of the corresponding x-ray detector 110-1, 110-2, 110-3, it would be possible for the position specification to be set in respect of one of the detector holders 112-1, 112-2 in which the corresponding x-ray detector 110-1, 110-2, 110-3 is affixed. By way of example, the corresponding detector holder 112-1, 112-2 could also comprise a corresponding identification number.

Different effects can be achieved by storing the status information 190-0, 190-1, 190-2, 190-3 in the database 101b. Thus, in general, it is possible to design a registration process of an x-ray detector 110-1, 110-2, 110-3 to the base station 101 in a manner that is comparatively robust in respect of errors and quick. Furthermore, ambiguities within the scope of operating the x-ray device 100 which emerge from the fact that a plurality of x-ray detectors 110-1, 110-2, 110-3 can be registered simultaneously to the base station 101 can be avoided; operating errors can be reduced as a result thereof. Furthermore, what can be achieved by having the various items of status information 190-0, 190-1, 190-2, 190-3 available in the database 101b is that connectivity problems between the various x-ray detectors 110-1, 110-2, 110-3 can be solved by operating the x-ray device 100 in an error mode, which resorts to the various items of status information 190-0, 190-1, 190-2, 190-3, or an incorrect operation on account of these connectivity problems can be prevented. What is common to all these effects is that an unnecessary radiation exposure of the subject due to an incorrect operation becomes less likely. Safety during the operation of the x-ray device 100 can be increased thereby.

By way of example, the status information 190-0, which comprises the identification number of the respective x-ray detector 110-1, 110-2, 110-3, can be received by the transceiver 110d of the base station 101 from the corresponding x-ray detector 110-1, 110-2, 110-3 by way of the further wireless interface 152 within the scope of the registration process of the various x-ray detectors 110-1, 110-2, 110-3 at the base station 101.

In particular, as depicted in FIG. 4, the range 152a of the further wireless interface 152 can be shorter than the range 151a of the wireless interface 151. By way of example, the wireless interface 151 could transfer data in a bidirectional manner and operate on the basis of WLAN technology. By way of example, the further wireless interface 152 could be selected from the following group: infrared, Bluetooth, NFC, optical transfer of machine-readable signs. The further wireless interface 152 can be unidirectional or bidirectional.

For the purposes of registering an x-ray detector 110-1, 110-2, 110-3 to the base station 101, the user of the x-ray device 100 can position the former within the range 152a of the further wireless interface 152, i.e. comparatively close to the base station 101, such that the status information 190-0 with the identification number then can be transferred from the x-ray detector 110-1, 110-2, 110-3 to the base station 101 by way of the further wireless interface 152. Then, the status information 190-0 with the identification number can be stored in the database 101b of the base station 101. By way of example, in order to carry out a verification of the transferred status information 190-0, this status information 190-0, furthermore, can be transmitted back to the corresponding x-ray detector 110-1, 110-2, 110-3 by way of the wireless interface 151. Acknowledgment of the registration can be carried out by way of the user interface 102.

By means of such techniques it is possible to dispense with, in particular, a manual input of the identification number of the x-ray detector 110-1, 110-2, 110-3 to be registered, as a result of which the registration process can be designed in a manner that is simpler and less prone to errors. The deregistration process could be realized by way of corresponding techniques.

By way of example, the machine-readable sign could be attached to a surface of the x-ray detector 110-1, 110-2, 110-3 and, within the scope of the registration/deregistration process, it is positioned within the field of view of a camera of the base station 101 such that the corresponding status information 190-0 can be acquired optically and evaluated.

Figure 5:
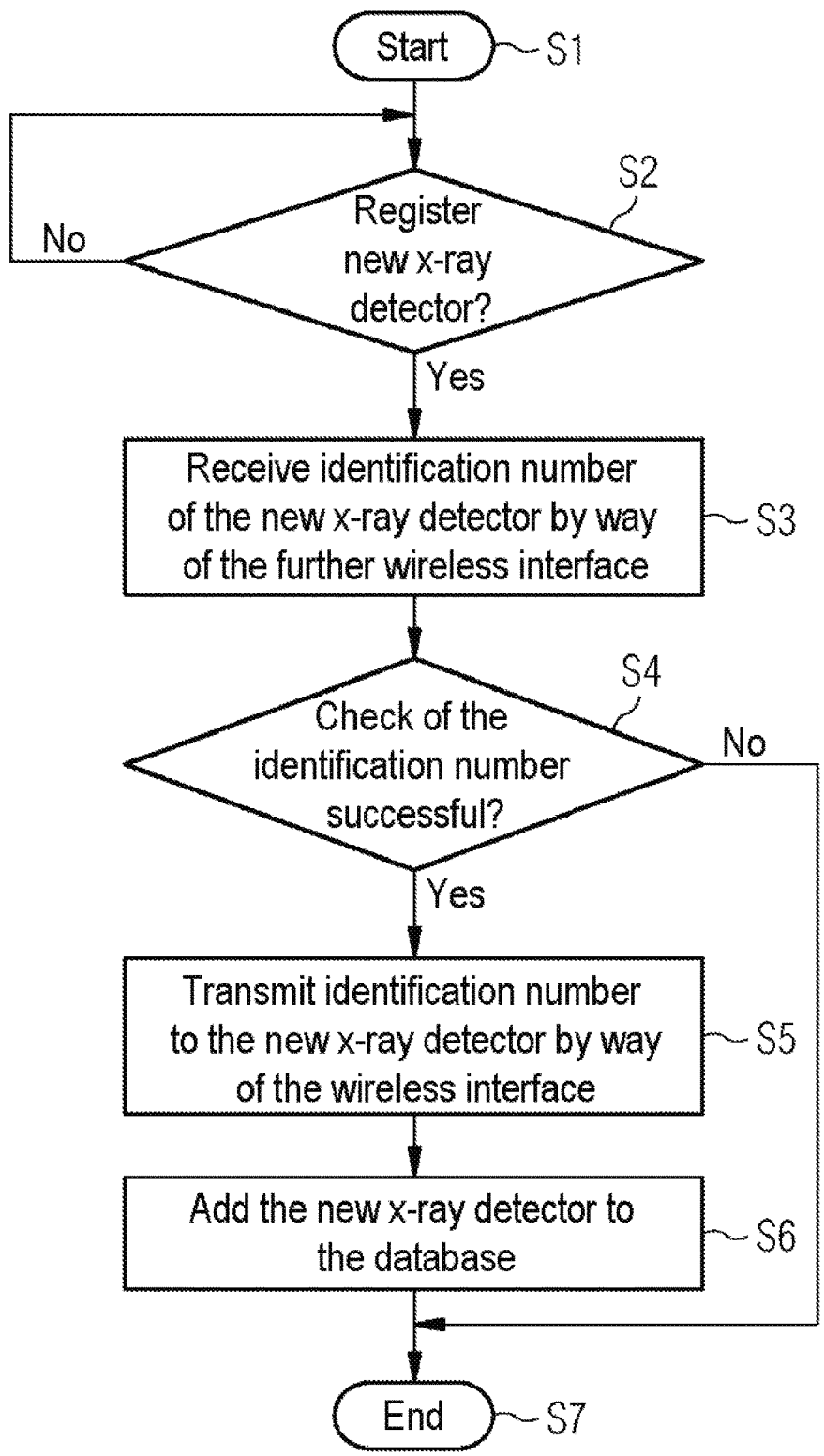
FIG. 5 is a flowchart of a method in accordance with various embodiments of the invention, which illustrates a registration process of an x-ray detector to the base station.

A flowchart relating to a registration process of an x-ray detector 110-1, 110-2, 110-3 to the base station 101 is depicted in FIG. 5. The method starts in step S1. In step S2, a check is carried out as to whether an x-ray detector 110-1, 110-2, 110-3 is intended to be registered. By way of example, step S2 can comprise the reproduction of an appropriate dialog by way of a monitor of the user interface 103. By way of example, the registration process can be started in step S2 following an appropriate user input.

If it is determined in step S2 that a new x-ray detector is intended to be registered to the base station 101, the method continues with step S3. In step S3, the identification number of the x-ray detector to be registered is received by way of the further wireless interface 152 as corresponding status information 190-0. To this end, it may be necessary for the user to position the x-ray detector 110-1, 110-2, 110-3 to be registered in the close vicinity of the base station 101 since the further wireless interface 152 has a comparatively short range 152a.

The identification number of the x-ray detector 110-1, 110-2, 110-3 to be registered is checked in step S4. By way of example, a check can be carried out within the scope of step S4 as to whether the corresponding identification number is already stored in the database 101b, i.e. whether the x-ray detector 110-1, 110-2, 110-3 to be registered is in fact already registered to the base station 101.

If the identification in step S4 is unsuccessful, the method terminates in step S7. Otherwise, for verification purposes, the identification number is transmitted from the base station 101 to the x-ray detector 110-1, 110-2, 110-3 to be registered by way of the wireless interface 151 (step S5). Step S5 can be denoted as an acknowledgment of the registration process.

The corresponding entry for the newly registered x-ray detector 110-1, 110-2, 110-3 is stored in the database 101b in step S6. By way of example, this can relate to storing the status information 190-0, which comprises the obtained identification number, in the database 101b. Then, the method terminates in step S7.

Figure 6:
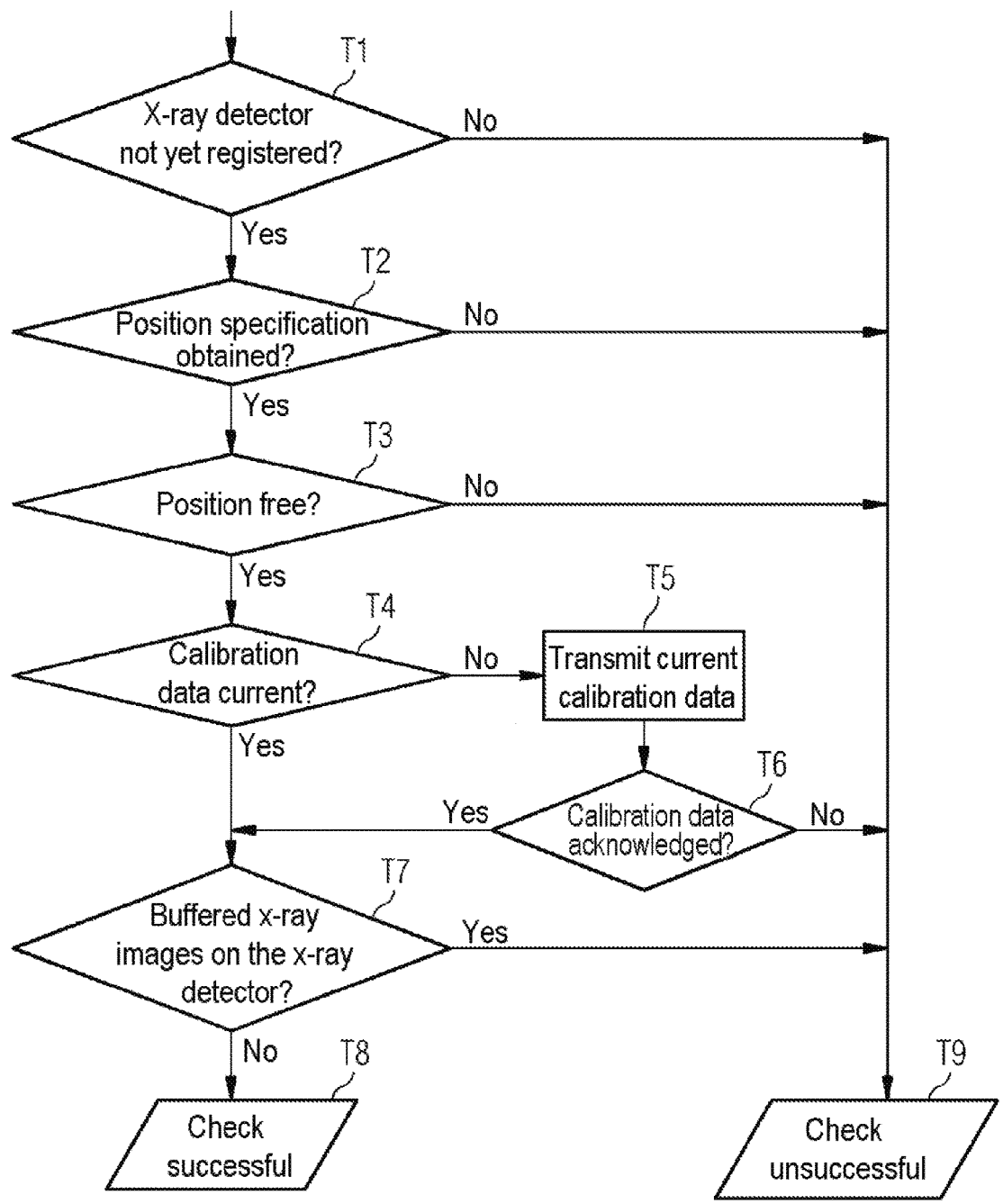
FIG. 6 is a flowchart which illustrates details of the flowchart in FIG. 5.

Further checks can be carried out in step S4. The various checks which can be optionally carried out within the scope of step S4 are depicted in more detail in the flowchart of FIG. 6. Initially, a check can be carried out in step T1 as to whether the x-ray detector 110-1, 110-2, 110-3 to be registered is in actual fact not yet registered to the base station 101. By way of example, this can be carried out by comparing the identification numbers obtained with the identification numbers already stored in the database 101b.

In step T2, a check is carried out as to whether an item of status information relating to position specification was obtained for the x-ray detector 110-1, 110-2, 110-3 to be registered, for example by way of a user input obtained by way of the user interface 103. A user could also be requested to input the position specification.

If the position specification is available, a check is carried out in step T3 as to whether the corresponding position is still available, i.e. whether another x-ray detector 110-1, 110-2, 110-3 is not already present at the position specified by the position specification. By way of example, the position specification can be specified in respect of one of the detector holders 112-1, 112-2. Step T3 can comprise a comparison of the corresponding status information in the database 101b.

A check as to whether the calibration data of the x-ray detector 110-1, 110-2, 110-3 to be registered are current and/or suitable is carried out in step T4. Optionally, calibration metadata can also be used to this end. The calibration data may be necessary for correct image acquisition within the scope of the acquisition of the x-ray image. If the calibration data are not current or unsuitable, current and suitable calibration data are transmitted from the base station 101, for example by way of the wireless interface 150, to the x-ray detector 110-1, 110-2, 110-3 to be registered. Subsequently, a check as to whether the calibration data are acknowledged is carried out in step T6. If the calibration data are acknowledged in step T6 or if the calibration data are determined to be still current and suitable in step T4, the method continues in step T7.

A check as to whether buffered x-ray images are stored on the x-ray detector 110-1, 110-2, 110-3 to be registered is carried out in step T7. If this is not the case, the check is considered successfully completed in step T8. Otherwise, the check is unsuccessful (step T9).

Above, it was predominantly techniques in relation to the registration process to the base station 101 of an x-ray detector 110-1, 110-2, 110-3 to be registered that were discussed. Below, it is predominantly scenarios in which an x-ray detector 110-1, 110-2, 110-3 was successfully registered to the base station 101 and in which an x-ray image is intended to be acquired by means of the x-ray detector 110-1, 110-2, 110-3 that are discussed.

Figure 7:
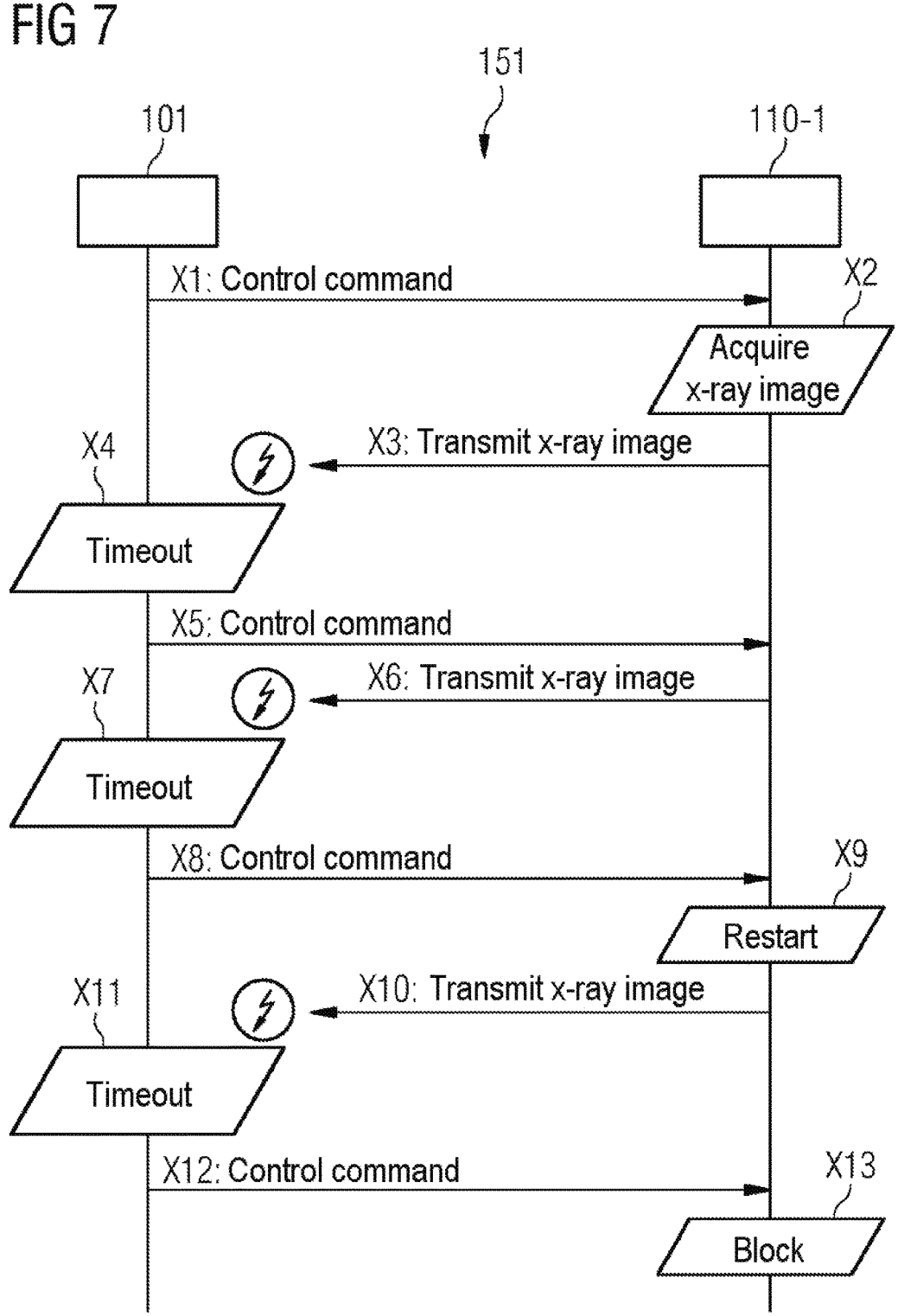
FIG. 7 is a signal flowchart over the wireless interface between the base station and an x-ray detector.

FIG. 7 shows a signal flowchart of the wireless interface 151 for such a scenario. Initially, a control command is transmitted from the base station 101 to the x-ray detector 110-1 by way of the wireless interface 151 (step X1). The control command initiates the acquisition of an x-ray image (step X2) by the x-ray detector 110-1. In step X3, the x-ray image is transmitted from the x-ray detector 110-1 to the base station 101.

In step X3, the transmission of the x-ray image fails, for example because the transfer quality of the wireless interface 151 is not sufficiently high such that the comparatively large file of the x-ray image cannot be transferred successfully (restricted connectivity). The failure of the transfer of the x-ray image in step X3 is determined by the base station 101 by a timeout (step X4). In this respect, alternative techniques could be used as well, such as e.g. an error log of the wireless interface 151, which is based on acknowledgments.

After the failure of the transfer of the x-ray image was determined in step X4, a control command which requests the renewed transmission of the x-ray image from step X2 from the x-ray detector 110-1 by way of the wireless interface 151 is transmitted to the x-ray detector 110-1 by way of the wireless interface 151 in step X5. In reaction thereto, the x-ray detector 110-1 re-transmits the x-ray image (step X6), which fails. This is identified in turn by the base station 101 (step X7).

Therefore, a further control command which re-initializes the x-ray detector 110-1 is transmitted to the at least one x-ray detector 110-1 (step X8). Upon reception of the control command in step X8, the x-ray detector 110-1 carries out a restart for re-initialization purposes (step X9). Then, the x-ray detector 110-1 re-transmits the x-ray image (step X10). What the re-initialization may achieve is the rectification of possible error causes for the multiple failure of the transmission (steps X3 and X6). However, in the example of FIG. 7, the x-ray image cannot be transferred, even after the re-initialization.

After checking whether the detected x-ray image is received by way of the wireless interface 151, which once again yields that there is an error in the transfer (step X11), a further control command which blocks the x-ray detector in respect of future registrations to base stations 101 is transmitted to the x-ray detector 110-1 in step X12. At the same time, a user of the x-ray device 100 can be requested, for example, to contact a service technician. The block is carried out in step X13.

The iterative transmission of control commands (steps X5, X8, X12) as a reaction to determining a failed transfer of the x-ray image (steps X4, X7, X12) can correspond to the operation of the x-ray device in an error mode which serves to improve the connectivity between the base station 101 and the x-ray detector 110-1.

Figure 8:
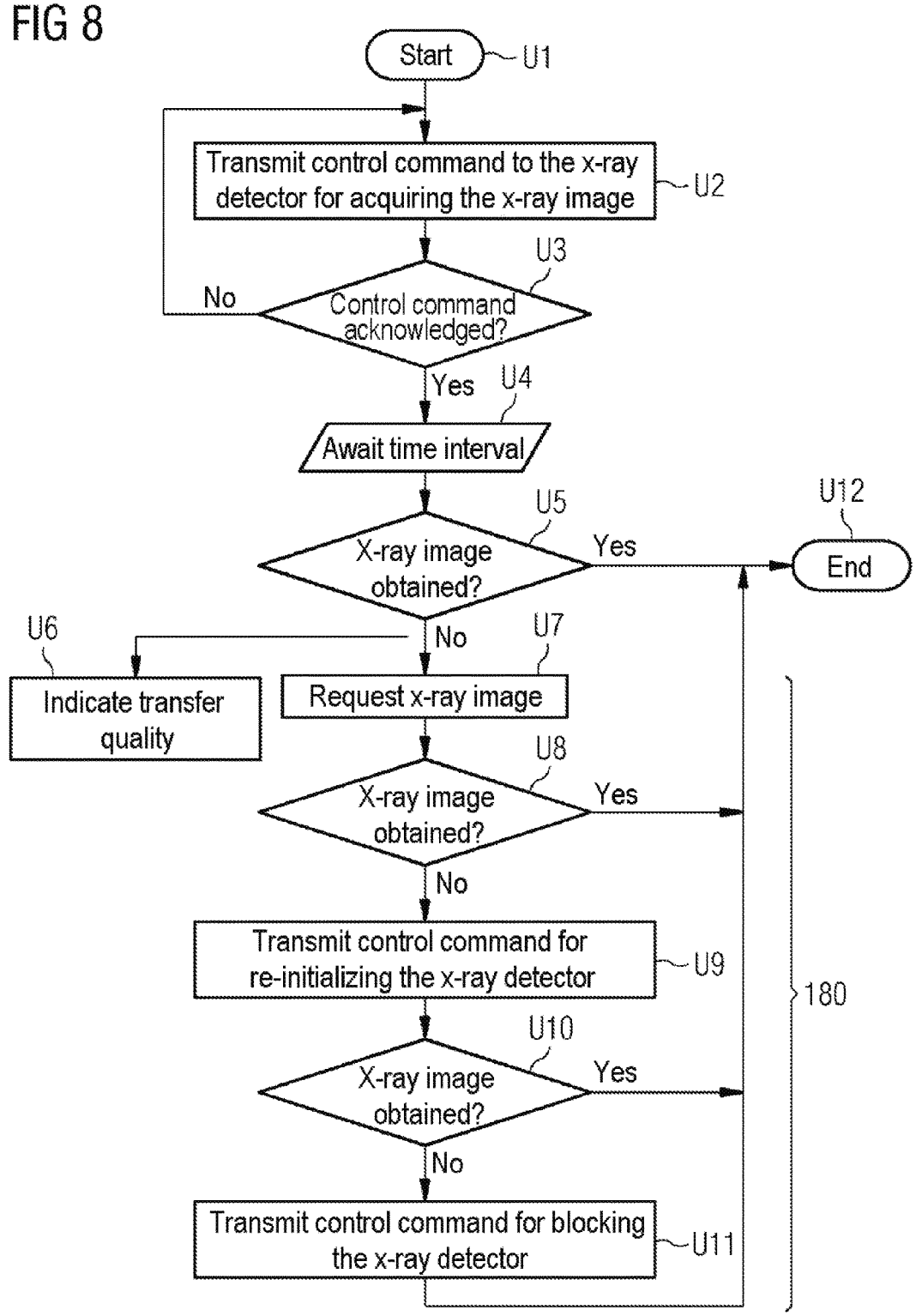
FIG. 8 is a flowchart of a method in accordance with the various embodiments of the invention, which illustrates an error mode.

Corresponding techniques are also depicted in the flowchart of FIG. 8. The method starts in step U1. Initially, a control command for acquiring the x-ray image is transmitted to the x-ray detector 110-1 in step U2. In step U3, a check is carried out as to whether this transmitted x-ray command is acknowledged. If there was no acknowledgment, step U2 is carried out again, otherwise the method continues with step U4. By way of example, acknowledgment can be brought about by way of an appropriate acknowledgment message.

A time interval is initially awaited in step U4 and a check as to whether the x-ray image was obtained is carried out in step U5. If the x-ray image was obtained in step U5, the method ends in step U12.

Otherwise, the x-ray device 100 is operated in the error mode 180. In the error mode 180, the x-ray image is initially requested again by way of a further control command (step U7). Once again, an acknowledgment of the transmitted control command can be obtained (this is not depicted in FIG. 8). Then, a check is carried out in step U8 as to whether the x-ray image was obtained now, for example once again after a specific time interval after step U7. If this is the case, the error mode 180 is terminated and the method ends in step U12.

If the x-ray image was not obtained in step U8, a further control command for re-initializing the x-ray detector 110-1 is transmitted (step U9). Once again, a check is carried out in step U10 as to whether the x-ray image was obtained, for example once again after a specific time interval after step U9. If the x-ray image was obtained in step U10, the error mode 180 is terminated and the method ends in step U12. However, if the x-ray image was not obtained, a control command is transmitted to the x-ray detector 110-1 in step U11 for the purposes of blocking the x-ray detector 110-1. The x-ray detector is then blocked in respect of further use by a user of the x-ray device 100. What this can prevent is a subject from being exposed to radiation exposure without it being possible to obtain an x-ray image as a result of the possibly defective x-ray detector 110-1.

Naturally, the various checks or the transmission of control commands, as were discussed above in conjunction with FIGS. 7 and 8, also can be carried out repeatedly.

By way of example, it would be possible for steps U7 and U8 to be carried out repeatedly in succession and for there to be a continuation with step U9 only after a specific time interval was awaited.

If the x-ray device 100 is operated in the error mode 180, i.e. if the upshot of step U5 is that the x-ray image was not obtained successfully, the status information 190-0-190-4, which comprises a transfer quality of the wireless interface 151, can be re-obtained. This transfer quality can be output to the user of the x-ray device 100 by way of the user interface 103. What this can achieve is that the user can increase the transfer quality, for example by corresponding repositioning of the x-ray detector 110-1 closer to the base station 101, such that the connectivity by way of the wireless interface 151 is reestablished. Accordingly, status information 190-0, 190-1, 190-2, 190-3 comprising a number of buffered and acquired x-ray images in the x-ray detector 110-1 and/or a status of an acquisition process of the x-ray image can be received by the x-ray detector 110-1 by way of the wireless interface 151 in the error mode 180. The corresponding information could be reproduced for a user within the scope of step U6. As a result of this, finding the error source of the restricted connectivity between the base station 101 and the x-ray detector 110-1 can be rendered possible for the user.

Figure 9:
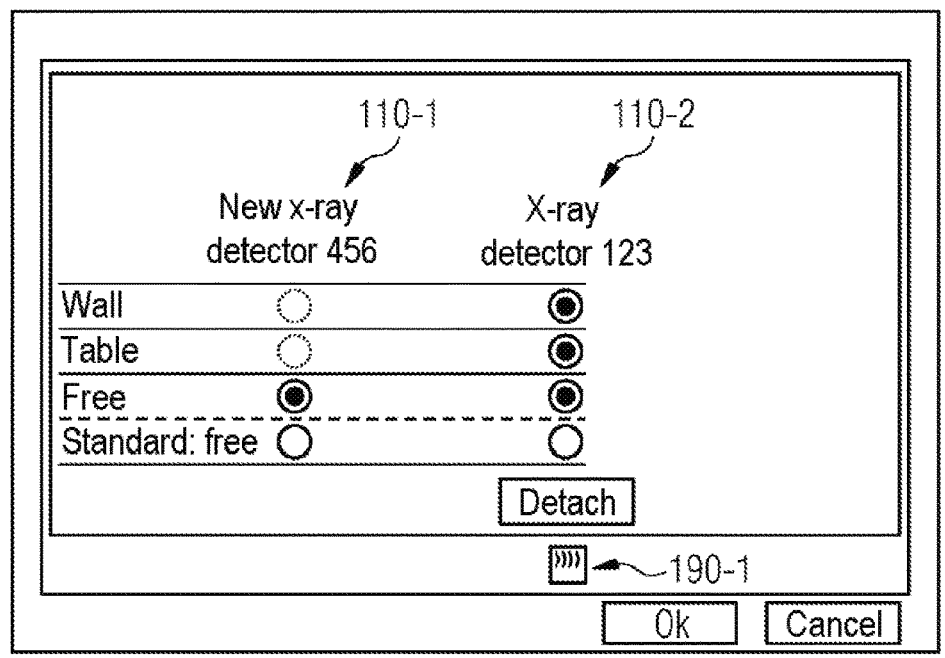
FIG. 9 illustrates a dialog box of a user interaction in accordance with various embodiments.

By way of example, a user interaction with the user of the x-ray device 100 can be carried out within the scope of controlling the x-ray device 100, wherein the user interaction comprises the depiction of status information 190-0, 190-1, 190-2, 190-3 from the database 101b on a monitor of the user interface 103 and/or the obtaining of status information by a user input by way of the user interface 103. FIG. 9 depicts a dialog box of the user interaction for registering a new x-ray detector 110-1 with the identification number "456". The user can select a position specification. By way of example, the user can select whether the x-ray detector 110-1 with the identification number "456" to be registered is positioned at the detector holder 112-1, 112-2 at the wall or at the table or whether it is a free x-ray detector, i.e. an x-ray detector 110-1, 110-2, 110-3, which is portable in free space and movable.

The x-ray detector 110-2 with the identification number "123" is already registered to the base station 101 and it could be deregistered by way of a user input. The transfer quality within the scope of the status information 190-1 is also indicated in the dialog box for the x-ray detector 110-2.

Figure 10:
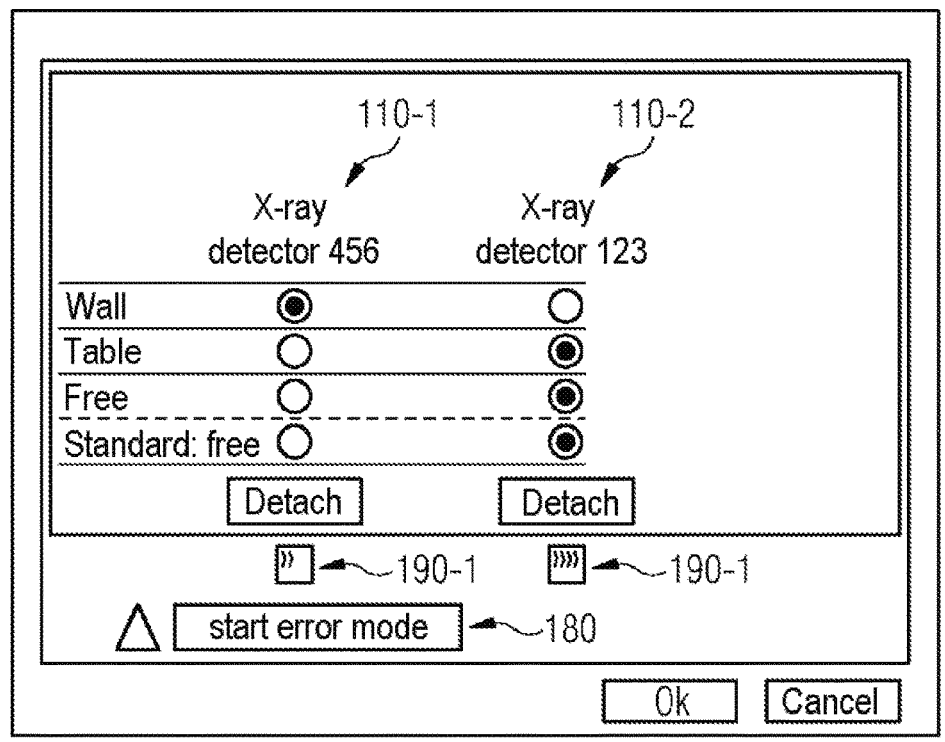
FIG. 10 illustrates a dialog box of a user interaction in accordance with various embodiments.

FIG. 10 shows a dialog box of the user interaction, in which both x-ray detectors 110-1, 110-2 are registered to the base station 101. Because the transfer quality, as illustrated by the status information 190-1 in the dialog box, is comparatively low for the x-ray detector 110-1 with the identification number "456", it is also possible to start the error mode 180 by way of a user input.

Figure 11:
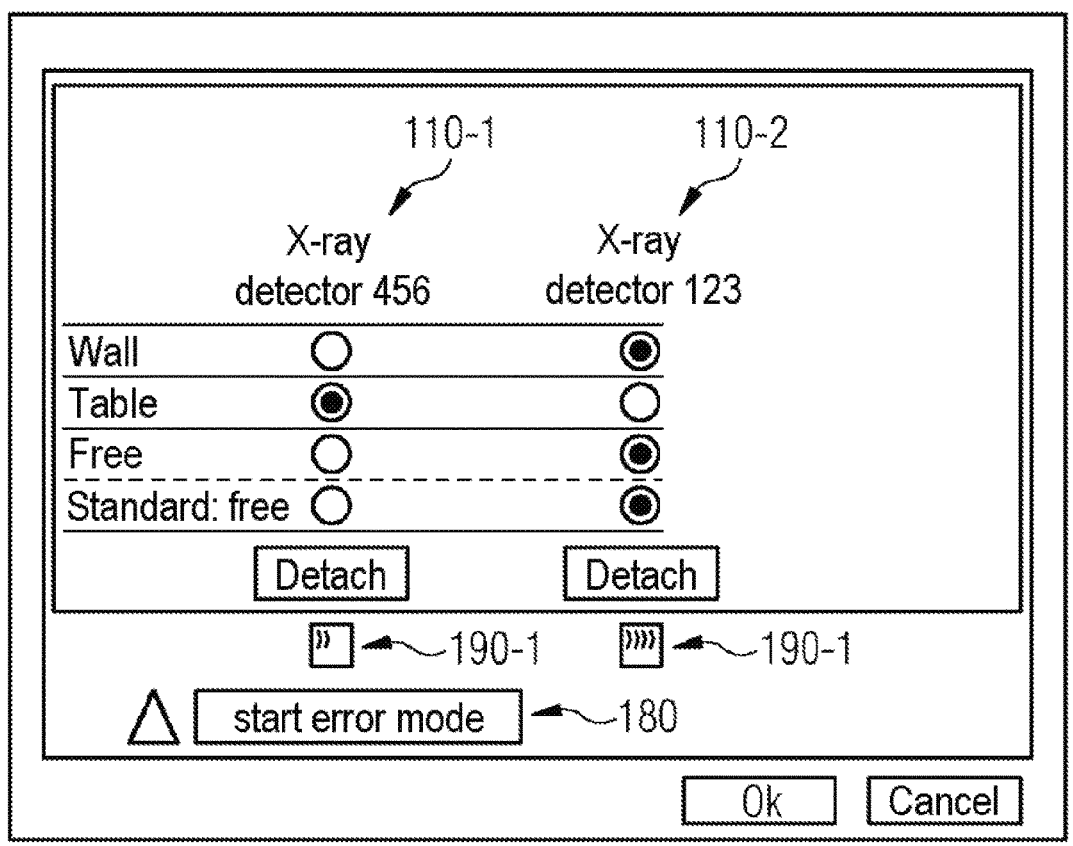
FIG. 11 illustrates a dialog box of a user interaction in accordance with various embodiments.

FIG. 11 depicts a corresponding situation. What emerges from comparing FIGS. 10 and 11 is that the position specification for the two x-ray detectors 110-1, 110-2 was modified by way of the user input. By way of example, such changes in the status information in the database 101b can be monitored and the corresponding information can be output to a user in the case of changes in the status information in the database 101b.

Naturally, the features of the embodiments and aspects of the invention, described above, can be combined with one another. In particular, the features can be used not only in the combinations described above, but also in other combinations or on their own, without departing from the field of the invention.

LIST OF REFERENCE SIGNS

100 X-ray device
110-1 X-ray detector
110-2 X-ray detector 110-3 X-ray detector
101 Base station
101a Computer unit
101b Database
101c Transceiver
101d Further transceiver
102 X-ray source
103 User interface
112-1 Detector holder
112-2 Detector holder
151 Wireless interface
151a Range
152a Range
152 Further wireless interface
180 Error mode
190-0 Status information
190-1 Status information
190-2 Status information
190-3 Status information

The invention claimed is:

1. A method for controlling an x-ray device having a base station and at least one x-ray detector, the base station configured to receive an acquired x-ray image from the x-ray detector by way of a wireless interface, which method comprises the following steps of:
providing the x-ray device with a further wireless interface differing from the wireless interface and having a smaller range than the wireless interface;
obtaining status information about the at least one x-ray detector by receiving the status information from the at least one x-ray detector by way of the further wireless interface within a scope of a registration process of the at least one x-ray detector to the base station, the status information relating to an operating parameter of the at least one x-ray detector;
storing the status information in a database of the base station, the database having at least one entry for each one of the at least one x-ray detector;
controlling the x-ray device on a basis of the status information from the database, the status information containing an identification number of the at least one x-ray detector;
transmitting a control command to the at least one x-ray detector by way of the wireless interface, the control command requests transmission of an x-ray image from the x-ray detector by way of the wireless interface; and
depending on a transmission of the control command, checking whether the acquired x-ray image is received by way of the wireless interface, and if the acquired x-ray image is not received operating the x-ray device in an error mode in respect of the at least one x-ray detector, the error mode serves to improve a connectivity between the base station and the at least one x-ray detector.

2. The method according to claim 1, wherein within the scope of the registration process of the at least one x-ray detector to the base station, performing the further step of transmitting the status information, which contains the identification number of the at least one x-ray detector, to the at least one x-ray detector by way of the wireless interface.

3. The method according to claim 1, which further comprises selecting the further wireless interface from the group consisting of infrared, Bluetooth, near field communication, and optical transmission of machine-readable signs.

4. The method according to claim 1, wherein:
the status information contains a position specification of the at least one x-ray detector;
the at least one x-ray detector is portable; and
the position specification is set in respect of a detector holder, in which the portable x-ray detector can be affixed.

5. The method according to claim 1, which further comprises selecting the status information from the group consisting of a battery charge state of the at least one x-ray detector, a number of buffered and acquired x-ray images in the at least one x-ray detector, a status of an acquisition process of the x-ray image, a transmission quality of the wireless interface, calibration data, calibration metadata, the identification number of the at least one x-ray detector, a position specification of the at least one x-ray detector, and a detector type of the at least one x-ray detector.

6. The method according to claim 1, which further comprises transmitting a further control command to the at least one x-ray detector if the x-ray device is operated in the error mode in relation to the at least one x-ray detector, the control command blocks the at least one x-ray detector in respect of future registrations to base stations and/or re-initializes the at least one x-ray detector.

7. The method according to claim 1, wherein if the x-ray device is operated in the error mode in relation to the at least one x-ray detector, repeating reception of the status information which includes a transmission quality of the wireless interface and an output of a transmission quality to a user.

8. The method according to claim 1, which further comprises receiving the status information from the at least one x-ray detector by way of the wireless interface if the x-ray device is operated in the error mode in relation to the at least one x-ray detector, the status information includes a number of buffered and acquired x-ray images in the at least one x-ray detector and/or a status of an acquisition process of the x-ray image.

9. The method according to claim 1, wherein the controlling step further comprises carrying out a user interaction, the user interaction includes depicting the status information from the database on a monitor and/or obtaining the status information by a user input.

10. The method according to claim 1, which further comprises monitoring for changes in the status information from the database, and in a case of changes in the status information from the database outputting corresponding information to a user.

11. An x-ray device, comprising:
at least one x-ray detector;
a wireless interface;
a further wireless interface differing from said wireless interface and having a smaller range than said wireless interface;
a base station configured to receive an acquired x-ray image from said x-ray detector by way of said wireless interface, said base station having a database and a computer unit configured to carry out the following steps:
obtain status information about said at least one x-ray detector by receiving the status information from said at least one x-ray detector by way of said further wireless interface within a scope of a registration process of said at least one x-ray detector to said base station, the status information relates to an operating parameter of said at least one x-ray detector;
store the status information in said database of said base station, said database having at least one entry for each one of said at least one x-ray detector;

control said x-ray device on a basis of the status information from said database, the status information having an identification number of said at least one x-ray detector;

transmit a control command to said at least one x-ray detector by way of said wireless interface, the control command requests transmission of an x-ray image from said x-ray detector by way of said wireless interface; and depending on a transmission of the control command, check whether the acquired x-ray image is received by way of said wireless interface, and if the acquired x-ray image is not received operating said x-ray device in an error mode in respect of said at least one x-ray detector, the error mode serves to improve connectivity between said base station and said at least one x-ray detector.

12. The x-ray device according to claim 11, wherein said x-ray device is configured to carry out a method according to claim 1.

* * * * *